US010527597B2

(12) United States Patent
Krauss

(10) Patent No.: US 10,527,597 B2
(45) Date of Patent: Jan. 7, 2020

(54) METHOD AND DEVICE FOR DETERMINING THE CARBON DIOXIDE CONTENT IN AMBIENT AIR

(71) Applicant: Robert Bosch GmbH, Stuttgart (DE)

(72) Inventor: Andreas Krauss, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/125,912

(22) PCT Filed: Feb. 2, 2015

(86) PCT No.: PCT/EP2015/052056
§ 371 (c)(1),
(2) Date: Sep. 13, 2016

(87) PCT Pub. No.: WO2015/135692
PCT Pub. Date: Sep. 17, 2015

(65) Prior Publication Data
US 2017/0003258 A1 Jan. 5, 2017

(30) Foreign Application Priority Data
Mar. 13, 2014 (DE) ......................... 10 2014 204 625

(51) Int. Cl.
*G01N 33/00* (2006.01)
*G01N 21/3504* (2014.01)
(Continued)

(52) U.S. Cl.
CPC .......... *G01N 33/004* (2013.01); *G01N 21/274* (2013.01); *G01N 21/3504* (2013.01);
(Continued)

(58) Field of Classification Search
CPC .. G01N 21/274; G01N 21/3504; G01N 21/61; G01N 33/0006; G01N 33/004
See application file for complete search history.

(56) References Cited

U.S. PATENT DOCUMENTS 4,609,058 A * 9/1986 Sashiki ................ G01G 19/393
177/1
2003/0134427 A1 7/2003 Chad et al.
(Continued)

FOREIGN PATENT DOCUMENTS

CN 1148172 A 4/1997
CN 101915747 A 12/2010
(Continued)

OTHER PUBLICATIONS

Vaisala, "Vaisala CARBOCAP (R) Sensor for Measuring Carbon Dioxide," available at http://www.vaisala.com/Vaisala%20Documents/Technology%20Descriptions/CEN-G-CARBOCAP-Technology-description-B210780EN.pdf, accessed Dec. 6, 2016 (2 pages).
(Continued)

*Primary Examiner* — David Z Huang
(74) *Attorney, Agent, or Firm* — Maginot, Moore & Beck LLP

(57) ABSTRACT

A method for determining the carbon dioxide content in ambient air includes providing a mobile data transmission device which comprises a sensor configured to detect carbon dioxide in ambient air. The method further includes calibrating the sensor. Calibrating the sensor includes measuring the carbon dioxide content of the ambient air in a reference situation. The method also includes measuring the carbon dioxide content of the ambient air using the sensor.

14 Claims, 2 Drawing Sheets

(51) Int. Cl.
*G01N 21/27* (2006.01)
*G01N 21/61* (2006.01)
*H04M 1/02* (2006.01)

(52) U.S. Cl.
CPC ......... *G01N 21/61* (2013.01); *G01N 33/0006* (2013.01); *G01N 2201/0221* (2013.01); *G01N 2201/127* (2013.01); *H04M 1/02* (2013.01); *H04M 2250/12* (2013.01)

(56) References Cited

U.S. PATENT DOCUMENTS

| | | |
|---|---|---|
| 2007/0005267 A1 | 1/2007 | Li |
| 2011/0009764 A1 | 1/2011 | Lanier et al. |
| 2012/0123287 A1 | 5/2012 | Gedeon |
| 2013/0038895 A1* | 2/2013 | Govyadinov ...... H04N 1/00204 358/1.15 |
| 2013/0174646 A1 | 7/2013 | Martin |
| 2015/0233879 A1* | 8/2015 | Tolmie ............... G01N 33/0006 128/202.22 |
| 2015/0300670 A1* | 10/2015 | Sakamoto ............ F24F 11/0017 165/237 |

FOREIGN PATENT DOCUMENTS

| | | |
|---|---|---|
| CN | 102822662 A | 12/2012 |
| CN | 103328954 A | 9/2013 |
| CN | 103512926 A | 1/2014 |
| WO | 2010045295 A1 | 4/2010 |
| WO | 2015030648 A1 | 3/2015 |

OTHER PUBLICATIONS

CEN, EN 13779, "Ventilation for non-residential buildings—Performance requirements for ventilation and room-conditioning systems," 2007 (72 pages).

International Search Report corresponding to PCT Application No. PCT/EP2015/052056, dated May 26, 2015 (German and English language document) (8 pages).

Vaisala; Vaisala CARBCAP Sensor for Measuring Carbon Dioxide; 2 Pages; www.vaisala.com.

Yasuda et al.; Comparison of the Characteristics of Small Commercial NDIR CO2 Sensor Models and Development of a Portable CO2 Measurement Device; Sensors; Mar. 16, 2012; pp. 3641-3655; vol. 12; www.mdpi.com/journal/sensors.

Oletic et al.; Empowering smartphone users with sensor node for air quality measurement; Journal of Physics: Conference Series 450, Sensors & their Applications XVII; 2013; 6 Pages; IOP Publishing Ltd.

Honicky et al.; N-SMARTS: Networked Suite of Mobile Atmospheric Real-time Sensors; NSDR'08; Aug. 18, 2008; pp. 25-29.

* cited by examiner

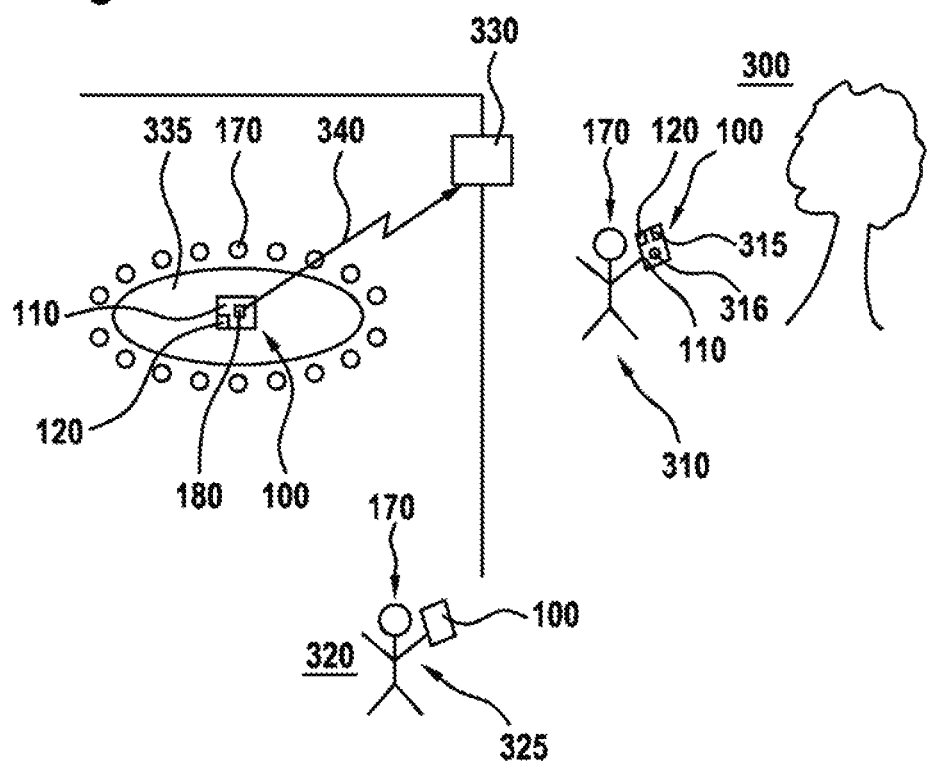
Fig. 3
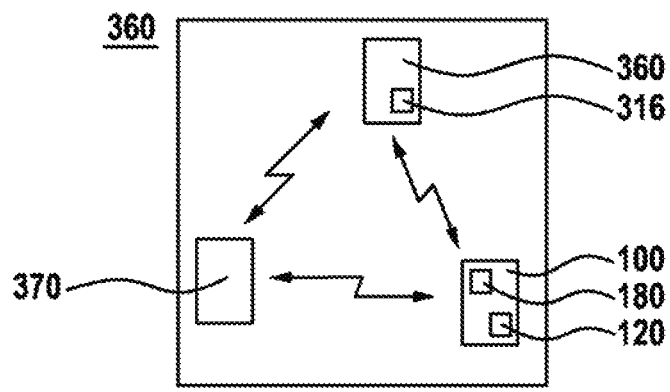

METHOD AND DEVICE FOR DETERMINING THE CARBON DIOXIDE CONTENT IN AMBIENT AIR

This application is a 35 U.S.C. § 371 National Stage Application of PCT/EP2015/052056, filed on Feb. 2, 2015, which claims the benefit of priority to Serial No. DE 10 2014 204 625.4, filed on Mar. 13, 2014 in Germany, the disclosures of which are incorporated herein by reference in their entireties.

BACKGROUND

The present disclosure relates to a method for determining a carbon dioxide content of ambient air, to a corresponding device and to a corresponding computer program.

The predominant use of $CO_2$ sensors can be seen in ventilation and air-conditioning technology for the purpose of controlling ventilation systems depending on requirements (see, for example, the Carbocap sensors from www.vaisala.de) and in safety technology, for example for the purpose of monitoring the tightness of $CO_2$-operated dispensing systems or fermentation cellars or cooling systems.

Typical $CO_2$ contents are between 380 ppm to several thousand ppm in air; according to DIN EN 13779, there are four quality levels: good up to 800 ppm, average and moderate quality between 800 and 1400 ppm (0.08 to 0.14% by volume), low room air quality above 1400 ppm; the maximum immission concentration is 3000 ppm (0.3%) and the maximum workplace concentration for a daily exposure of eight hours per day is 5000 ppm=0.5%.

In recent years, virtually only NDIR measuring methods have become established for measuring $CO_2$ in ambient air, but these measuring methods all require an adsorption section of several cm and changes in the IR source and influences of other gases must also be compensated for by means of a referencing method. There are also sensors on the market which measure the air quality by means of broadly sensitive sensors, for example from the company Applied-Sensor which offers metal-oxide-based sensors for measuring $CO_2$ equivalents (see, for example, http://www.applied-sensor.com/pdfs/APS_iAQ2000_0310.pdf). These sensors are not sensitive to $CO_2$ at all, but rather measure the air quality and therefore indirectly also the $CO_2$ concentration using other gases which are likewise produced when a room is used and which are also perceived as unpleasant.

SUMMARY

The various forms of air quality sensors are fitted in a stationary manner in all known applications and are often very far away from the direct ambient air which is relevant to the person in an auditorium or a conference room, for example. Communication between the sensor and the ventilation system is indeed already partially carried out in a wireless manner, in particular in the field of building technology, but only to facilitate installation (lower amount of assembly effort, permanently laid cables are dispensed with). The sensors are still fastened in a stationary manner to a wall or ceiling or in an exhaust air duct, for example.

Mobile telephones are equipped with a multiplicity of sensors, in particular GPS and inertial sensors, but the future use of pressure sensors and moisture sensors is also foreseeable. Mobile telephones can be easily networked, even using local radio connections, and are also predominantly in the vicinity of the owner.

Against this background, the approach presented here is used to present a method for determining a carbon dioxide content of ambient air as well as a device which uses this method and finally a corresponding computer program according to the following description. Advantageous configurations emerge from the subsequent description.

A method for determining a carbon dioxide content of ambient air is disclosed in the present case, wherein the method has the following steps of:
providing a mobile data transmission device which has a sensor for recording carbon dioxide in ambient air; and
measuring a carbon dioxide content of the ambient air using the sensor.

Ambient air can be understood as meaning air which is around the data transmission device having the sensor. A mobile data transmission device may be understood as meaning, for example, a transmitting and receiving unit for transmitting data in a bidirectional manner. For example, such a mobile data transmission device may be a mobile telephone or a tablet computer. A sensor can be understood as meaning a measuring sensor which is able to directly or indirectly record a carbon dioxide content or proportion in the ambient air and to provide a corresponding signal.

The approach presented here is based on the knowledge that a mobile data transmission device which typically has already achieved great market penetration can be very easily used for an additional function, namely the determination of the carbon dioxide content of the ambient air. In this case, use can be made of the fact that the mobile data transmission device is usually held or operated very close to the body of a user, but at least closer than conventional sensors for a carbon dioxide content in the ambient air. This makes it possible to record a measured value for the carbon dioxide content of the ambient air which is considerably more precise and more meaningful for the well-being of the person or the user than a measured value which has been recorded by a carbon dioxide sensor arranged in a stationary manner (usually on a room ceiling). The approach presented here therefore provides the advantage of making it possible to considerably improve the use of a mobile data transmission device by cost-effectively integrating only a small additional sensor, which is technically simple to produce, in such a data transmission device.

An embodiment of the approach presented here which has a step of calibrating the sensor is favorable. Such an embodiment of the approach presented here provides the advantage of providing precise measured values for the carbon dioxide content of the ambient air, even in situations in which the measurement properties of the sensor are changed owing to ageing or when an unfavorable or varying measurement environment for measuring the carbon dioxide content in the ambient air is present.

The approach presented here can be carried out in a particularly simple manner according to an embodiment in which, in the calibration step, a carbon dioxide content of the ambient air is measured in a reference situation representing a situation having a carbon dioxide content within a tolerance range around a reference value. Such a reference situation may be present, for example, when the sensor is charged with ambient air which is taken from outside, for example in a park or away from relatively large crowds of people. Such an embodiment of the approach presented here provides the advantage that the carbon dioxide content of the ambient air in the reference situation is well known as a reference value from empirical values, with the result that the presence of the reference situation during calibration can be clearly and quickly detected if the carbon dioxide content which is within a tolerance range (of 10%, for example) around this reference value is measured by the sensor.

An embodiment of the present disclosure in which, in the calibration step, the presence of the reference situation is detected using a camera and/or a noise sensor is also advantageous. Such an embodiment of the present disclosure provides the advantage of a reference situation which is technically very easy to detect.

According to another embodiment of the approach presented here, in the calibration step, a position of the sensor and/or of the data transmission device can be recorded and/or read in, wherein the presence of the reference situation is detected using the position. Using such a position, which represents a geographical location of the mobile data transmission device or of the sensor for example, makes it possible to very easily check or verify whether the mobile data transmission device or the sensor is in the first reference situation.

In the calibration step, the position can also be recorded using a wireless position detection system and/or wherein the reference value can be changed using the position which has been recorded and/or read in. Such an embodiment of the approach presented here provides the advantage that the position is determined using means which are usually already present as standard in a data transmission device. This makes it possible to determine the position very cost-effectively and quickly. Alternatively or additionally, the position can provide an indication of whether the mobile data transmission device or the sensor is in an environment in which the reference value differs from a reference value at another position. This makes it possible to take into account, for example, whether the mobile data transmission device or the sensor is in a pedestrian zone of a city center (with little air exchange and therefore possibly an increased carbon dioxide content), a highway parking lot (with an increased carbon dioxide content on account of the traffic traveling on the highway) or in an open field (with a lot of air exchange and therefore possibly a normal or low carbon dioxide content). It is therefore possible to increase the calibration accuracy of the sensor by adapting the reference value according to the position which has been recorded or read in.

An embodiment of the approach presented here in which, in the calibration step, a carbon dioxide content of the ambient air is measured in a further reference situation representing a situation having a carbon dioxide content within a further tolerance range around a further reference value is particularly advantageous. In this case, in particular, the further reference value may represent a higher carbon dioxide content of the ambient air than the reference value. Such an embodiment of the approach presented here provides the advantage that the sensor can be adjusted to different measurement points or operating points by using the further reference situation having the further reference value, with the result that a measurement dynamics profile of the sensor also be advantageously calibrated.

The calibration in the further reference situation can be carried out in a particularly simple manner if, in the calibration step, air exhaled by a person is used as ambient air for the purpose of determining the further reference situation. Since the carbon dioxide content of air exhaled by a person in the alveolar volume is very precisely known from medical investigations and such air exhaled by persons is also easily and quickly available when the mobile data transmission device or sensor is used by the user, the further reference situation can be created very easily and cost-effectively, in particular if the presence of alveolar air can be determined with the aid of further sensors.

A technically very simple determination of whether the calibration is currently being carried out in the reference situation or the further reference situation can be carried out, according to one embodiment of the approach presented here, when, in the calibration step, the presence of the reference situation and/or of the further reference situation is determined using a moisture and/or a temperature of the ambient air and/or using measured values from a motion, acceleration, acoustic and/or optical sensor. This makes it possible to advantageously use the fact that, if the further reference situation is present, the (exhaled air as) ambient air used has a high moisture content and almost body temperature, whereas, when the reference situation is present, the mobile data transmission device or the sensor is used outdoors, for example, and therefore experiences a high incidence of light or relatively strong accelerations or movements. This makes it possible to reliably distinguish different reference situations using technically very simple aids, with the result that precise calibration is enabled. Image recognition can also be used to detect the reference situation in an automated or supportive manner or as a control. A reference situation in clear outside air with a low $CO_2$ concentration, for instance, can be detected using the visibility of trees or predominantly blue sky or using the absence of faces as an indication of little exhaled air or else using further sensors, for example with little background noise corresponding to little traffic.

In order to ensure that a value which is as accurate as possible can be determined for the carbon dioxide content of the ambient air, in the calibration step, the carbon dioxide content of the ambient air can be recorded according to one embodiment of the approach presented here when a measured value for the carbon dioxide content of the ambient air does not change by more than a deviation amount within a predefined period. For example, such a predefined period may comprise a period of 5 seconds in which a measured value for the carbon dioxide content of the ambient air does not change by more than the deviation amount (of 10%, for example). Such an embodiment of the approach presented here provides reliable calibration of the sensor by using a steady-state measured value in a corresponding reference situation.

According to another embodiment of the approach presented here, a step of requesting calibration is provided, wherein the execution of the calibration step is requested in the requesting step when a manually input calibration request signal is read in, when a predefined calibration repetition period. has elapsed, and/or when a carbon dioxide content signal recorded by a further sensor represents a carbon dioxide content of the ambient air which deviates from the carbon dioxide content recorded using the sensor by more than a differential amount. Such an embodiment of the approach presented here provides the advantage of flexible calibration depending on whether the calibration is intended to be activated manually or can be carried out on the basis of particular parameters such as a particular time or a change in external signals.

An embodiment of the approach presented here in which a step of outputting a control signal to a ventilation unit, in particular wherein the control signal is output using the mobile data transmission device, is particularly advantageous. In this case, the control signal can be output, in particular, on the basis of a carbon dioxide content of the ambient air measured by the sensor, for example if the measured carbon dioxide content falls below a predefined threshold value. Such an embodiment of the approach presented here provides the advantage of being able to influence the composition of the ambient air, for example by switching on (or switching off) the (venting) ventilation unit, and hereby improving the well-being or health of users of the mobile data transmission device having the sensor. At the same time, a transmitting/receiving interface usually present as standard mobile data transmission device can continue to be used in a cost-effective manner, in particular by using the mobile data transmission device to output control signal.

Another embodiment of the approach presented here also provides a device which is designed to carry out and/or control all steps of a method according to a variant presented here. In particular, such a device may be a device for determining a carbon dioxide content of ambient air, which device has a mobile data transmission device and a sensor for recording carbon dioxide in ambient air. Alternatively or additionally, the device may also have a unit for controlling measurement of a carbon dioxide content of the ambient air using the sensor.

The approach presented here therefore provides a device which is configured to carry out or implement the steps of a variant of a method presented here in corresponding apparatuses. The object on which the disclosure is based can also be quickly and efficiently achieved by means of this embodiment variant of the disclosure in the form of a device.

In the present case, a device can be understood as meaning an electrical device which processes sensor signals and outputs control and/or data signals on the basis thereof. The device may have an interface which may be designed using hardware and/or software. In the case of a hardware design, the interfaces may be, for example, part of a so-called system ASIC which comprises a wide variety of functions of the device. However, it is also possible for the interfaces to be separate, integrated circuits or to at least partially consist of discrete components. In the case of a software design, the interfaces may be software modules which are present on a microcontroller in addition to other software modules, for example.

A computer program product or computer program having program code which may be stored on a machine-readable carrier or storage medium, such as a semiconductor memory, a hard disk memory or an optical memory, and is used to carry out, implement and/or control the steps of the method according to one of the embodiments described above, in particular if the program product or program is executed on a computer or a device, is also advantageous. Therefore, the approach presented here provides a computer program which is set up to carry out and/or control all steps of a variant of a method described here. The approach proposed here also provides a machine-readable storage medium having a computer program according to a variant presented here stored thereon.

BRIEF DESCRIPTION OF THE DRAWINGS

The approach presented here is explained, by way of example, in more detail below using the accompanying drawings, in which:

FIG. 3 shows a schematic illustration of different usage or calibration situations of the device according to one exemplary embodiment of the present disclosure.

DETAILED DESCRIPTION

In the following description of favorable exemplary embodiments of the present disclosure, identical or similar reference symbols are used for the elements which are illustrated in the various figures and have a similar action, in which case a repeated description of these elements is dispensed with.

Figure 1:
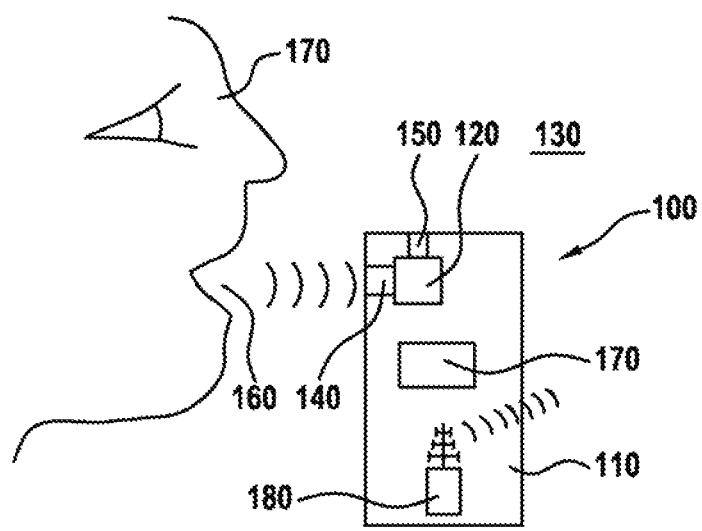
FIG. 1 shows a block diagram of a device according to one exemplary embodiment of the present disclosure.

FIG. 1 shows a block diagram of a device 100 for determining a carbon dioxide content of ambient air according to one exemplary embodiment of the present disclosure. The device 100, which can also be referred to as a carbon dioxide measuring system for example, comprises a mobile data transmission device 110. The mobile data transmission device 110 be a mobile telephone or a tablet computer, for example. A sensor 120 for recording carbon dioxide in ambient air 130 is integrated in this mobile data transmission device 110. For example, the sensor 120 may have an inlet channel 140 in order to draw in or generally receive ambient air 130 and also an outlet channel 150 in order to discharge evaluated (ambient) air from the sensor 120 again. In this case, the sensor 120 may be arranged, for example, in a region of the mobile data transmission device 110, with the result that it is also likewise easily possible to blow in air from the mouth 160 of a user 170 of the data transmission device 110 via the inlet channel 140. Therefore, the device 100 can be understood as meaning a mobile $CO_2$ measuring device in which a method for measuring the air quality and $CO_2$ (in particular using the mobile sensor system 100) can be carried out. In this case, the measured values can be locally transmitted on a display 170 of the device 100 and/or can be transmitted further using a transmitting and receiving apparatus 180.

Figure 2:
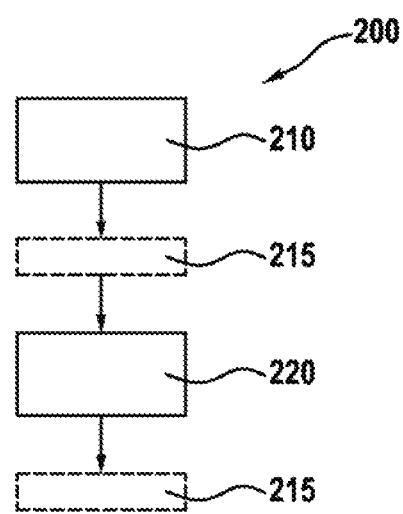
FIG. 2 shows a flowchart of a method according to one exemplary embodiment of the present disclosure.

FIG. 2 shows a flowchart of a method 200 for determining a carbon dioxide content of ambient air according to one exemplary embodiment of the present disclosure. The method 200 comprises a step 210 of providing a mobile data transmission device which has a sensor for recording carbon dioxide in ambient air and a step 220 of measuring a carbon dioxide content of the ambient air using the sensor. Alternatively or additionally, a calibration step 215 can be carried out before or after step 220 in order to set the sensor 120 of the device to a particular measurement point. A calibration process, as described in more detail with reference to FIG. 3 for example, can be used for this purpose.

FIG. 3 shows different usage scenarios of the use of the device 100, even during a calibration process. In a first situation 300, also referred to as a reference situation, the sensor 120 can be used to record a reference value for the carbon dioxide content of the ambient air if the device 100 is in a position 310 of the reference situation 300. FIG. 3 illustrates a position 310 outdoors, for example in a park, as the reference situation 300. In this reference situation 300, the carbon dioxide content of the ambient air (outdoors) is known from empirical values and is approximately 0.039% by volume, which can be used as the reference value for calibrating the sensor 120. In order to check whether the user 170 is also actually in the position 310 outdoors, it is possible to use, for example, a positioning system 315 (for example a satellite-based positioning system, such as GPS), for example in the form of recording the position of the geographical coordinates of the device 100 and checking whether these recorded coordinates are actually in an environment outdoors. This makes it possible to verify whether the calibration has actually been carried out in the reference position. A camera can likewise be used either on its own or additionally to check the environment for possibly interfering influences, for example exclusion of persons or other sources for $CO_2$, for example automobiles with a running engine in front of or in the vicinity of the device.

In a further reference situation 320, exhaled air which likewise contains a previously known carbon dioxide content of approximately 5.6% by volume can be applied to the sensor 120, for example. This further reference position can be effected at a further position 325 which may also, however, be identical to the position 310. This known value of the exhaled air can then be used as a further reference value for calibrating the sensor 120. This further reference situation can therefore also be used to obtain a measurement point for calibrating the sensor 120. Recording the moisture and/or temperature of the exhaled air as ambient air 130 of the device now likewise again makes it possible to verify whether the exhaled air has actually been applied to the sensor 120 and a valid calibration measurement has therefore been carried out in the further reference position 320.

The device 100 can also be used to control a venting system 330. For example, the device 100 may be placed on a table 335 in a conference room and can record the carbon dioxide content of the ambient air in the conference room. If it is determined that the carbon dioxide content falls below a threshold value, the data transmission device 110 or a transmitting and receiving interface 180 of the latter, for example, can be used to output a control signal 340, for example, to the venting system 330 and to switch on the latter. This makes it possible to increase the supply of fresh air in the conference room, which contributes to improving the conference climate.

An intended purpose of the approach presented here can be assumed to be that of measuring the air quality at the actually relevant point in a room, namely in a mobile manner using sensors which are worn directly by the person or are close to the person. These sensors enable a local display on the mobile device or else the transmission of the values to a ventilation system, for example in buildings or motor vehicles, in order to thus ensure an optimum air quality for the person. In particular, the sensors are intended to be used in mobile telephones which, in addition to a display and a power supply, provide a plurality of communication paths for a connection and can already be networked as standard in the motor vehicle (hands-free apparatus), for example.

An important aspect of the disclosure presented here is the integration of gas sensors for measuring air quality as cumulative parameters or in the form of individual parameters, for example individual gas concentrations, in mobile devices which are worn by the owner on his body or are in the vicinity of the body and are, in particular, wirelessly networked or can be wirelessly networked, in particular in mobile telephones. A recalibration method which can be called up via the mobile device, for example, allows the use of compact $CO_2$ sensors which are suitable for mobile telephones, for example, and cannot be used without recalibration, for example on account of a drift behavior. The calibration method uses, for example, a plurality of gases with known or approximately known concentrations, in particular outside air having a low $CO_2$ concentration and exhaled air having a high $CO_2$ concentration.

The NDIR-based sensors which were described under the prior art and are intended to measure a $CO_2$ content are not suitable for integration in mobile telephones on account of the space required for the adsorption section. For use in mobile data transmission devices, such as the data transmission devices proposed here, the typical space requirements for a sensor 120 are in the region of an edge length of less than 3 mm and a height of less than 2 mm. These requirements result in the need to use other sensor principles in the sensor 120 proposed here, for example based on the adsorption of $CO_2$ on or in adsorption materials, for example polymers which react as a base, and reading the properties changed thereby, for example a changed mass, viscosity or electrical properties such as permittivity or resistance. The optical measurement of $CO_2$ in a suitable enhancement material is likewise conceivable. Most methods have partially been known for decades from the literature and the sensors which can be produced therewith at low cost are very small and have a low power consumption.

In comparison with NDIR methods, however, all methods have worse stability properties and require a larger amount of recalibration effort. The cause is, on the one hand, the change in the adsorption material over time, in particular as a result of the effects of contaminants from the air (for example solvents), or else the adsorption of moisture in high concentrations, which masks the $CO_2$ adsorption.

These measurement principles for $CO_2$ can now be used for mobile use, for example by means of the calibration method. The calibration method uses a two-point calibration, in particular for $CO_2$, in which case the concentrations of the $CO_2$ are respectively known or approximately known. The calibration method can be called up automatically, for example at regular intervals of time, or by the user.

A calibration point with a low $CO_2$ concentration which is close to the natural background of typically 0.039% by volume can be effected if the mobile telephone is exposed in clean outside air. The GPS sensor can be used to determine whether the mobile telephone is directly in the outside air and to determine the whereabouts. Correction values for a locally increased $CO_2$ background can therefore be read from a $CO_2$ map stored on a data server, for example, for the global distribution, on the one hand, or else, on the other hand, for example, for densely populated areas such as cities (locally dynamic concentration values which take into account the wind dependence, for example, can therefore possibly be used. If necessary, the globally increasing background concentration of $CO_2$ can likewise be taken into account). The instantaneous use of the telephone can be read from a position and movement pattern of the inertial sensors present in the telephone and from camera data, data from distance sensors and taking into account the data transmission used. A constant, relatively large distance from the body is ideal for measuring a background value for $CO_2$ in order to obtain values which have not been changed by exhaled air. This is the case, for example, when using the mobile telephone for Internet access together with operation via the touchscreen. Alternatively, a reference measurement can also be requested by the user, in which case the user is requested to leave the telephone at a distance from the body for some time in air which is as clear as possible (for example in a park in an urban area). In this case, the reaching of a constant $CO_2$ concentration at the sensor can be read using the sensor itself. As soon as the measured value is stable, the background concentration of $CO_2$ can be assigned to this measured value as part of recalibration. The recording of the temperature and moisture using a further sensor can likewise be included in the recalibration or can prevent the recalibration in the event of excessively high or excessively low values.

The second calibration, point for the $CO_2$ calibration can be determined by using exhaled air. When the end-expiratory or alveolar air volume is used, this air has a constant $CO_2$ value of approximately 5.6% by volume in most people. In a similar manner to that in an alcohol test, the user should exhale deeply in a uniform manner in order to reach the value of the end-expiratory volume. This uniform exhalation can be qualitatively recorded, for example using an acoustic signal such as a microphone signal, for example using parameters such as the exhalation duration or the uniformity of the air flow. With an appropriate arrangement, for example in the form of a Pitot tube, a barometric pressure sensor can be used to measure the necessarily uniform and deep exhalation. A fast reacting moisture sensor (ideally with a time-limited temperature increase in order to prevent condensation on the sensor; alternatively or additionally, it is also possible to calibrate or check the moisture sensor at the same time under these conditions) can likewise be used to measure the temperature and moisture of the exhaled air which should be almost at 37° C. and should have complete moisture saturation if the calibration method is carried out correctly. The reaching of a constant value of the $CO_2$ concentration can likewise be determined using the uncalibrated $CO_2$ sensor in a continuous measurement. The concentration achieved during exhalation can be displayed initially in relative units as a profile curve on a display device. A constant value reached at the end of the exhalation process can then be used for quantitative recalibration.

Measured values from further sensors, for example pressure sensors or temperature sensors, can be used to calculate absolute values, for example partial pressures for $CO_2$, or to carry out further plausibility tests.

Simplified measurements such as capnometry or capnography can then be carried out with a calibrated $CO_2$ sensor 120 using the above additional functions (above-mentioned flow measurement via a microphone and/or a pressure sensor). Further information, relating to the ventilation (lung function), hemodynamics and metabolism of a user can then possibly be calculated on the basis of these results and can be achieved and displayed by means of comparison from a database with results from other users.

Although the upper calibration point at 5.6% by volume of $CO_2$ is somewhat outside the measurement range relevant to room air quality, it can be assumed that the sensor should reliably record these $CO_2$ values since breathing on the mobile telephone can be considered to be normal user behavior and can therefore be expected.

With a somewhat linear sensor behavior, a compensated and acceptable error for the $CO_2$ measurement can be expected for the relevant entire measurement range for room air.

When the approach described above is used to control a ventilation system, information obtained from other sensors, for example acceleration sensors or a camera 316, for example, can be used to determine the position of the mobile sensor system, for example if the sensor system in the form of the mobile telephone is, during a discussion, on the table in the vicinity of the discussion participants. Alternatively, the user can be requested to place the mobile telephone onto the table for a measurement if the mobile device detects an interface to a ventilation or air-conditioning system controller, for example a Bluetooth connection inside a room.

The same applies to the motor vehicle; in this case, a holder provided in the interior can possibly be used for the mobile sensor. It is possible to query whether the sensor is in the holder, for example from an electrical connection (charging plug). If there are a plurality of mobile sensors 100 and, in particular, if in connection to stationary, calibrated sensors 360 inside a space, a plurality of values can be used by the air-conditioning system controller; sensors with values which deviate greatly from measured values from other sensors can possibly be excluded from the evaluation. In addition, the greatly deviating sensors can be informed that the values deviate and that recalibration should be carried out.

The relative sensor signals can likewise be purely evaluated by the ventilation controller by blowing fresh or outside air into the room or the motor vehicle, for example in the case of an initial very high ventilation level, and by assuming that the measured value resulting for this state is the value for good air quality. Subsequent measured values are then each evaluated only with respect to the change with regard to this initial measured value. This method can likewise be used if, for example, a room has been ventilated for a relatively long time without use (for example overnight) and sensors are then introduced into this room.

For calibration or a functional check, for example during production, this procedure can be expanded by a calibration apparatus predefining a gas concentration in a particular space, for example in a measurement chamber, in which one or more sensors 360 and/or 370 have been or are placed and wait until an equilibrium value (that is to say fluctuation of the determined value only within a narrow tolerance range) in the sensor signal is achieved. If a connection is established between the one or more sensors and the calibration apparatus, the current measured values can be transmitted from the sensor to the calibration apparatus and the predefined concentration can conversely be transmitted from the calibration apparatus to the sensors, whereupon the calibration apparatus or the sensors calculate(s) calibration values and store(s) them in the sensor.

The exemplary embodiments described and shown in the figures are selected only by way of example. Different exemplary embodiments can be combined with one another completely or with respect to individual features. An exemplary embodiment can also be supplemented with features from a further exemplary embodiment.

Furthermore, the method steps presented here can be carried out repeatedly and in a sequence other than the sequence described.

If an exemplary embodiment comprises an "and/or" conjunction between a first feature and a second feature, this can be read such that the exemplary embodiment has both the first feature and the second feature according to one embodiment and has either only the first feature or only the second feature according to a further embodiment.

The invention claimed is:

1. A method for determining a carbon dioxide content of ambient air, the method comprising:
   providing a mobile data transmission device which has a sensor configured to record carbon dioxide in ambient air;
   periodically performing a calibration process on the mobile data transmission device to calibrate the sensor, the calibration process including measuring a carbon dioxide content of the ambient air in a reference situation representing a situation having a carbon dioxide content within a tolerance range around a reference value; and
   measuring a carbon dioxide content of the ambient air using the sensor,
   wherein calibrating the sensor includes measuring a carbon dioxide content of the ambient air in a further reference situation representing a situation having a carbon dioxide content within a further tolerance range around a further reference value,
   wherein calibrating the sensor includes using air exhaled by a person as ambient air for determining the further reference situation, the air exhaled by a person being considered as having a carbon dioxide value of 5.6%, detecting or at least checking a presence of the reference situation by the mobile data transmission device using at least one further sensor of the data transmission device, wherein calibrating the sensor includes at least one of recording and reading in a position of at least one of the sensor and the data transmission device, wherein the presence of the reference situation is detected using the position, and wherein the presence of the reference situation is detected using at least one of a camera and a noise sensor.

2. The method as claimed in claim 1, wherein the position is recorded using a wireless position detection system.

3. The method as claimed in claim 2, further comprising changing the reference value using the position which has been recorded and/or read in.

4. The method as claimed in claim 1, wherein calibrating the sensor includes determining the presence of at least one of the reference situation and the further reference situation using at least one of: (i) at least one of a moisture and a temperature of the ambient air; and (ii) measured values from at least one of a motion sensor, an acceleration sensor, and an optical sensor.

5. The method as claimed in claim 1, wherein calibrating the sensor includes recording the carbon dioxide content of the ambient air when a measured value for the carbon dioxide content of the ambient air does not change by more than a deviation amount within a predefined period.

6. The method as claimed in claim 1, further comprising: requesting calibration when a predefined reference situation has been set.

7. The method as claimed in claim 6, wherein the predefined reference situation is at least one of window ventilation and ventilation of a room carried out using a ventilation system.

8. The method as claimed in claim 1, further comprising: outputting a control signal to a ventilation unit.

9. The method as claimed in claim 8, wherein the control signal is output using the mobile data transmission device.

10. The method as claimed in claim 1, wherein the method is carried out and/or controlled by a computer program comprising programmed instructions stored on a non-transitory computer readable storage medium.

11. The method as claimed in claim 1, further comprising changing the reference value using the position which has been recorded and/or read in.

12. The method as claimed in claim 1, wherein the further reference value represents a higher carbon dioxide content of the ambient air than the reference value.

13. A device for determining a carbon dioxide content of ambient air, the device comprising:
a mobile data transmission device including a sensor configured to record carbon dioxide in ambient air,
a wireless position detection system configured to detect a position of at least one of the sensor and the data transmission device, wherein:
the sensor is configured to periodically perform a calibration process that includes measuring a carbon dioxide content of the ambient air in a reference situation representing a situation having a carbon dioxide content within a tolerance range around a reference value, and
the sensor is configured to measure a carbon dioxide content of the ambient air,
wherein the calibration process includes measuring a carbon dioxide content of the ambient air in a further reference situation representing a situation having a carbon dioxide content within a further tolerance range around a further reference value,
wherein the calibration process includes using air exhaled by a person as ambient air for determining the further reference situation,
wherein the presence of the reference situation is detected using the position, and
wherein the presence of the reference situation is detected using at least one of a camera and a noise sensor.

14. A method for determining a carbon dioxide content of ambient air, the method comprising:
providing a mobile data transmission device which has a sensor configured to record carbon dioxide in ambient air;
periodically performing a calibration process on the mobile data transmission device to calibrate the sensor, the calibration process including measuring a carbon dioxide content of the ambient air in a reference situation representing a situation having a carbon dioxide content within a tolerance range around a reference value; and
measuring a carbon dioxide content of the ambient air using the sensor,
wherein calibrating the sensor includes measuring a carbon dioxide content of the ambient air in a further reference situation representing a situation having a carbon dioxide content within a further tolerance range around a further reference value,
wherein calibrating the sensor includes using air exhaled by a person as ambient air for determining the further reference situation,
wherein calibrating the sensor includes at least one of recording and reading in a position of at least one of the sensor and the data transmission device using at least one further sensor of the data transmission device,
wherein the presence of the reference situation is detected using the position, and
wherein the presence of the reference situation is detected using at least one of a camera and a noise sensor.

* * * * *